United States Patent
Hong et al.

(10) Patent No.: US 11,564,738 B2
(45) Date of Patent: Jan. 31, 2023

(54) USING PULMONARY VEIN ISOLATION FOR PATIENTS WITH ATRIAL FIBRILLATION

(71) Applicant: Biosense Webster (Israel) Ltd., Yokneam (IL)

(72) Inventors: Anthony Hong, Irvine, CA (US); Lee Ming Boo, Irvine, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 124 days.

(21) Appl. No.: 16/835,062

(22) Filed: Mar. 30, 2020

(65) Prior Publication Data
US 2020/0352642 A1    Nov. 12, 2020

Related U.S. Application Data

(60) Provisional application No. 62/843,779, filed on May 6, 2019.

(51) Int. Cl.
*A61B 18/00* (2006.01)
*A61B 18/14* (2006.01)
*A61B 18/12* (2006.01)

(52) U.S. Cl.
CPC ...... *A61B 18/1492* (2013.01); *A61B 18/1206* (2013.01); *A61B 2018/0022* (2013.01);
(Continued)

(58) Field of Classification Search
CPC ........... A61B 18/1492; A61B 18/1206; A61B 2018/00666; A61B 2018/0022;
(Continued)

(56) References Cited

U.S. PATENT DOCUMENTS

| 5,391,199 A | 2/1995 | Ben-Haim |
| 5,944,022 A | 8/1999 | Nardella et al. |

(Continued)

FOREIGN PATENT DOCUMENTS

EP    3351197 A1    7/2018

OTHER PUBLICATIONS

Schmidt EU, Schneider R, Lauschke J, Wendig I, Bänsch D. The HATCH and CHA2DS 2-VASc scores. Prognostic value in pulmonary vein isolation. Herz. May 2014;39(3):343-8. doi: 10.1007/s00059-013-3835-x. Epub May 18, 2013. PMID: 23681208. (Year: 2013).*

(Continued)

*Primary Examiner* — Jaymi E Della
(74) *Attorney, Agent, or Firm* — Frost Brown Todd LLP

(57) ABSTRACT

A method for ablating a patient, consisting of ascertaining a $CHA_2DS_2$-VASc score for the patient and inserting a probe into the patient, so as to contact a pulmonary vein of the patient. The method further includes applying energy via the probe so as to ablate the pulmonary vein until pulmonary vein isolation (PVI) is achieved. When PVI is achieved and the $CHA_2DS_2$-VASc score is less than a preset value, ablation of the pulmonary vein is ceased. When PVI is achieved and the $CHA_2DS_2$-VASc score is greater than or equal to the preset value, energy is applied to perform a further ablation.

18 Claims, 4 Drawing Sheets

(52) U.S. Cl.
CPC ............ *A61B 2018/00202* (2013.01); *A61B 2018/00357* (2013.01); *A61B 2018/00375* (2013.01); *A61B 2018/00577* (2013.01); *A61B 2018/00666* (2013.01)

(58) Field of Classification Search
CPC ........... A61B 2018/00357; A61B 2018/00375; A61B 2018/00577
See application file for complete search history.

(56) References Cited

U.S. PATENT DOCUMENTS

| | | | |
|---|---|---|---|
| 5,983,126 | A | 11/1999 | Wittkampf |
| 6,456,864 | B1 | 9/2002 | Swanson et al. |
| 6,690,963 | B2 | 2/2004 | Ben-Haim et al. |
| 6,892,091 | B1 | 5/2005 | Ben-Haim et al. |
| 2012/0209260 | A1* | 8/2012 | Lambert ............ A61B 18/1492 606/41 |
| 2013/0282004 | A1* | 10/2013 | Lesh .................. A61N 7/02 606/41 |
| 2014/0277070 | A1* | 9/2014 | Otero ............... A61B 17/12186 606/194 |
| 2017/0151008 | A1* | 6/2017 | Mazor ................ A61B 18/02 |
| 2017/0347896 | A1* | 12/2017 | Keyes ................ A61B 5/746 |

OTHER PUBLICATIONS

Link MS, Haïssaguerre M, Natale A. Ablation of Atrial Fibrillation: Patient Selection, Periprocedural Anticoagulation, Techniques, and Preventive Measures After Ablation. Circulation. Jul. 26, 2016;134(4):339-52. doi: 10.1161/CIRCULATIONAHA. 116. 021727. PMID: 27462054. (Year: 2016).*

Extended European Search Report dated Oct. 29, 2020, for Application No. 20173017.3, 8 pages.

* cited by examiner

United States Patent US 11,564,738 B2

USING PULMONARY VEIN ISOLATION FOR PATIENTS WITH ATRIAL FIBRILLATION

CROSS-REFERENCE TO RELATED APPLICATIONS

This application claims the benefit of priority from U.S. Provisional Patent Application Ser. No. 62/843,779, filed May 6, 2019, which Provisional Patent Application is hereby incorporated herein by reference as if set forth in full into this application.

FIELD OF THE INVENTION

This invention relates generally to atrial fibrillation, and specifically to treating the atrial fibrillation by pulmonary vein isolation and additional left atrial ablation.

BACKGROUND OF THE INVENTION

Pulmonary vein isolation (PVI) is the cornerstone of treating atrial fibrillation, and is used for both Paroxysmal AF (PAF) and Persistent AF (PsAF). However, while the results of PVI for patients with PAF are consistently good, the results for patients with PsAF are much more variable. Thus, some patients with PsAF do well with just PVI, while other patients in the category need more treatment than just PVI.

SUMMARY OF THE INVENTION

An embodiment of the present invention provides a method for ablating a patient, consisting of:
ascertaining a $CHA_2DS_2$-VASc score for the patient;
inserting a probe into the patient, so as to contact a pulmonary vein of the patient;
applying energy via the probe so as to ablate the pulmonary vein until pulmonary vein isolation (PVI) is achieved;
when PVI is achieved and the $CHA_2DS_2$-VASc score is less than a preset value, ceasing ablation of the pulmonary vein; and
when PVI is achieved and the $CHA_2DS_2$-VASc score is greater than or equal to the preset value, applying the energy to perform a further ablation.

In a disclosed embodiment the preset value is 1 if the patient is male, and is 2 if the patient is female.

In a further disclosed embodiment the probe includes a balloon catheter.

In a yet further disclosed embodiment the probe includes a focal catheter.

In an alternative embodiment the energy includes radio-frequency energy.

In a further alternative embodiment the further ablation is in proximity to the pulmonary vein. Typically the further ablation includes ablation of rotors and/or ablation to isolate a posterior atrial wall and/or ablation to isolate a left atrial appendage and/or ablation of an additional location of arrhythmogenic activity.

There is further provided, according to an embodiment of the present invention, apparatus for ablating a patient, including:
a probe, configured to be inserted into the patient, so as to contact a pulmonary vein of the patient;
and a processor, configured to:
ascertain a $CHA_2DS_2$-VASc score for the patient,
apply energy via the probe so as to ablate the pulmonary vein until pulmonary vein isolation (PVI) is achieved, cease ablation of the pulmonary vein when PVI is achieved and the $CHA_2DS_2$-VASc score is less than a preset value, and
apply the energy to perform a further ablation when PVI is achieved and the $CHA_2DS_2$-VASc score is greater than or equal to the preset value.

The present disclosure will be more fully understood from the following detailed description of the embodiments thereof, taken together with the drawings, in which:

DETAILED DESCRIPTION OF EMBODIMENTS

Overview

To date, typically for patients with persistent atrial fibrillation (PsAF), there has not been a tool that categorizes patients with atrial fibrillation as just needing PVI (pulmonary vein isolation), or needing more than just PVI.

The inventors have found that the $CHA_2DS_2$-VASc score for a patient may be used as a metric for determining whether PVI alone may be sufficient for the patient, or whether more treatment, i.e., further ablation outside of the pulmonary vein, may be required. (The score is described in detail in the Detailed Description of the Embodiments section below.) If the patient score is less than a preset value, which depends on the gender of the patient, then PVI alone may be sufficient to treat the atrial fibrillation of the patient. If the patient score is greater than or equal to the preset value, then further treatment, i.e. ablation other than PVI alone, may be necessary to treat the atrial fibrillation.

(It should be noted that the $CHA_2DS_2$-VASc score is at present used to predict/estimate the risk of stroke in patients with atrial fibrillation. A high score corresponds to a greater risk of stroke, so that typically in this case anticoagulation treatment is required.)

In an embodiment of the present invention a physician ascertains a $CHA_2DS_2$-VASc score for the patient. The physician then inserts a probe into the patient, and navigates the probe so that a distal end of the probe contacts a pulmonary vein of the patient.

The physician then uses the distal end to apply a suitable energy modality, typically radio-frequency energy or pulsed field ablation (also known as irreversible electroporation), to ablate the pulmonary vein so that pulmonary vein isolation is achieved. The achievement of pulmonary vein isolation is determined by the physician (who may also be the operator of the probe) usually with a mapping probe to detect for the absence of electrical signals conducted between the atrium and the subject vein or by pacing the coronary sinus and detecting entry block of signals. When the $CHA_2DS_2$-VASc score is less than the preset value referred to above, the physician may cease ablation of the pulmonary vein and withdraw the probe from the vein. When the $CHA_2DS_2$-VASc score is greater than or equal to the preset value, the physician may need to perform further ablation outside the vein. The physician typically performs the above procedure sequentially on all of the patient pulmonary veins.

DETAILED DESCRIPTION

Figure 1:
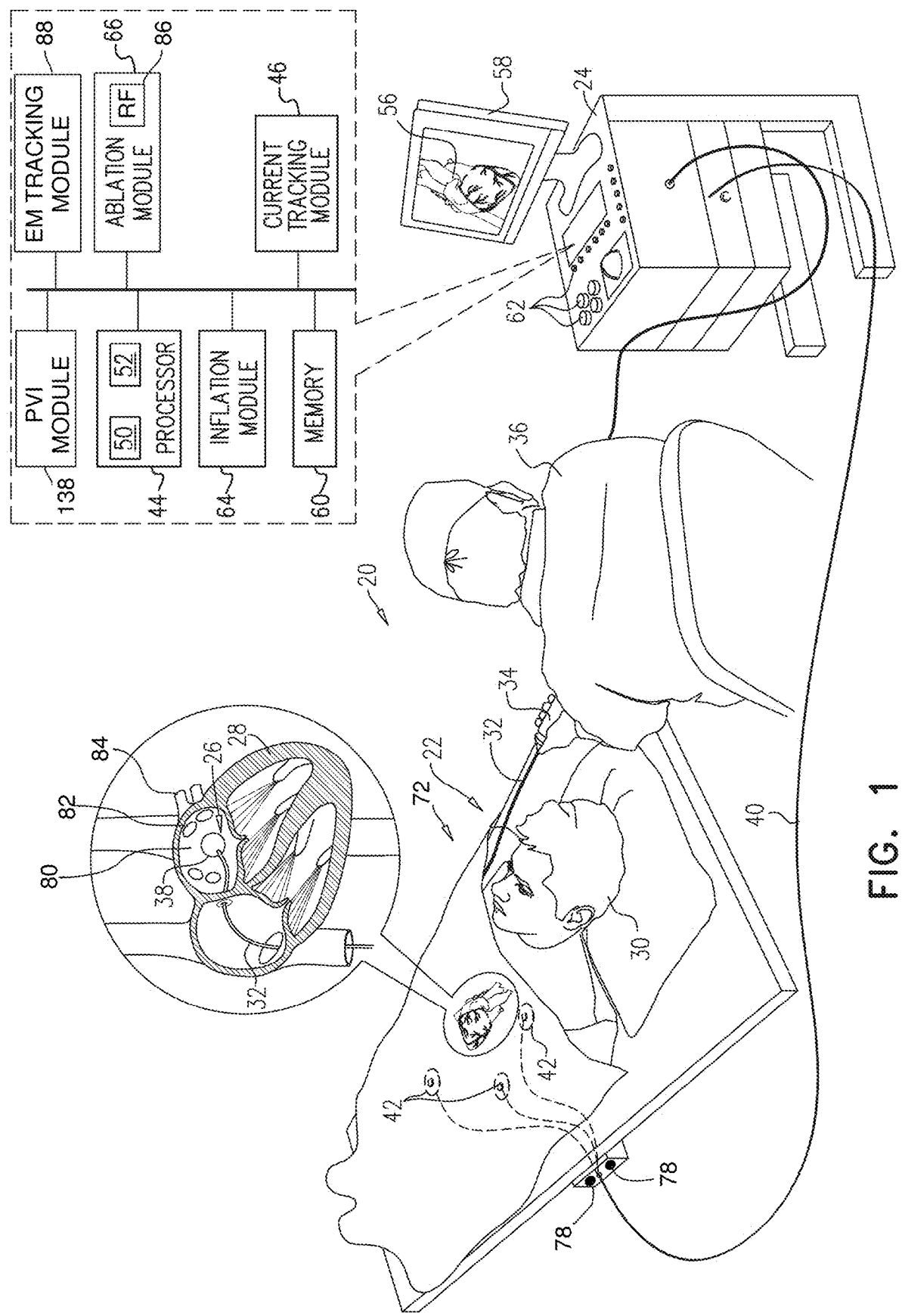
FIG. 1 is a schematic, pictorial illustration of a medical system, according to an embodiment of the present invention.
Figure 2:
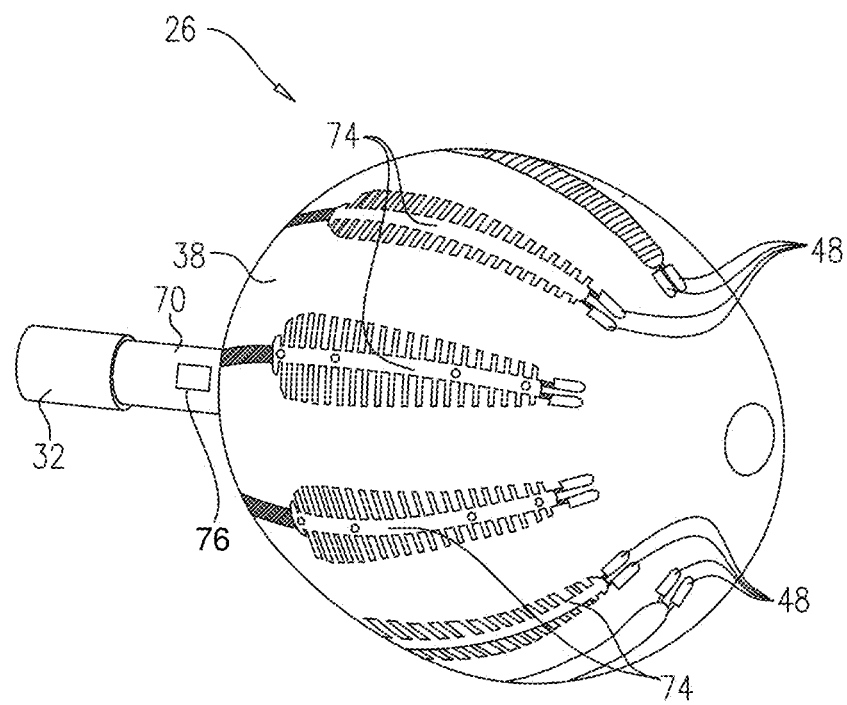
FIG. 2 is a schematic pictorial illustration of a distal end of a medical probe used in the system, according to an embodiment of the present invention.

FIG. 1 is a schematic, pictorial illustration of a medical system 20 comprising a medical probe 22 and a control console 24, and FIG. 2 is a schematic pictorial illustration of a distal end 26 of the medical probe, according to an embodiment of the present invention. Probe 22 is used as a catheter, and is also referred to herein as catheter 22. Medical system 20 may be based, for example, on the CARTO® system, produced by Biosense Webster Inc. of 33 Technology Drive, Irvine, Calif. 92618 USA. In embodiments described hereinbelow, medical probe 22 is used for ablation of tissue in a heart 28 of a patient 30 (also referred to herein as a subject). Alternatively, medical probe 22 may be used, mutatis mutandis, for other therapeutic and/or diagnostic purposes in the heart or in other body organs.

Probe 22 comprises an insertion tube 32 and a handle 34 coupled to a proximal end of the insertion tube. During a medical procedure, a medical professional 36 can insert probe 22, via a prepositioned sheath 72, through the vascular system of patient 30 so that distal end 26 of the medical probe enters a chamber of heart 28. Upon distal end 26 entering the chamber of heart 28, medical professional 36 can deploy a balloon 38, described in more detail below, that is affixed to distal end 26, and the medical professional can manipulate handle 34 to position the balloon in order to engage myocardial tissue at a desired location or locations. Balloon 38 is typically formed from bio-compatible material such as polyethylene terephthalate (PET), polyurethane, nylon, or silicone.

In the configuration shown in FIG. 1, control console 24 is connected, by a cable 40, to body surface electrodes, which typically comprise adhesive skin patches 42 that are affixed to patient 30. Control console 24 also comprises a processor 44 which is coupled to a number of modules, the modules comprising software and/or hardware components. Details and functionality of the modules are described below.

Processor 44, in conjunction with a current tracking module 46, determines location coordinates of distal end 26 inside heart 28 based on impedances and/or currents measured between adhesive skin patches 42 and microelectrodes 48 and/or ablation electrodes 74 (FIG. 2) that are affixed to balloon 38 (typically as gold overlaying the balloon). In addition to being used as location sensors during a medical procedure, microelectrodes 48 (also referred to herein simply as electrodes) may perform other tasks such as measuring electrical activity of heart 28 and/or pacing of the heart.

Alternatively or additionally, processor 44 determines location coordinates of distal end 26 based on signals received by an electromagnetic (EM) tracking module 88. The signals are generated by a magnetic sensor 76 incorporated into a tubular shaft 70 of distal end 26, and the sensor generates its signals in response to magnetic fields, transmitted by alternating magnetic field radiators 78 positioned beneath patient 30, traversing the sensor.

Processor 44 may comprise real-time noise reduction circuitry 50 typically configured as a field programmable gate array (FPGA), followed by an analog-to-digital (A/D) signal conversion integrated circuit 52. The processor can pass the signals from A/D circuit 52 to another processor and/or can be programmed to determine the location coordinates referred to above.

Impedance and current-based location tracking techniques are described, for example, in U.S. Pat. Nos. 5,983,126, 6,456,864, and 5,944,022. Electromagnetic location tracking techniques are described, for example, in U.S. Pat. Nos. 5,391,199, 6,690,963, and 6,892,091. The methods of location sensing described hereinabove are implemented in the above-mentioned CARTO® system and are described in detail in the patents cited above.

Prior to insertion of probe 22 into patient 30, processor 44 acquires an electroanatomical map 56 of heart 28. Typically data for the map is acquired using a probe other than probe 22, such as a focal catheter which is configured to be both tracked by module 46 and to acquire signals from regions of heart chambers contacted by the catheter. An example of a focal catheter is described below with reference to FIG. 3. Typically, although not necessarily, processor 44 uses the signals to determine local activation times (LATs) of the heart chambers, and incorporates the LATs into map 56. Map 56 is stored in a memory 60 accessible by processor 44, and during the procedure the processor can present map 56 to medical professional 36 on a display 58.

During the procedure using probe 22, processor 44 may overlay an icon, representing the location of distal end 26 (determined as described above) on map 56, so enabling professional 36 to track the distal end.

Memory 60 may comprise any suitable volatile and/or non-volatile memory, such as random access memory or a hard disk drive. In some embodiments, medical professional 36 can manipulate map 56 using one or more input devices 62. In alternative embodiments, display 58 may comprise a touchscreen that can be configured to accept inputs from medical professional 36, in addition to presenting map 56.

In the configuration shown in FIG. 2, balloon 38 (shown inflated) is affixed to tubular shaft 70 that terminates distal end 26. Balloon 38 is configured to extend from sheath 72, and to deploy into a left atrium 80 of heart 28 so that electrodes 74 contact an ostium 82 of a pulmonary vein 84. The contact may be verified by any convenient means known in the art, such as by noting a change of impedance between the electrodes and patches 42.

Control console 24 also comprises an inflation module and an ablation module 66. Ablation module 66 is configured to monitor and control ablation parameters such as the level and the duration of ablation power (e.g., radio-frequency (RF) energy) conveyed to ablation electrodes 74 from ablation module 66, and module 66 typically comprises an RF generator 86 for this purpose.

Inflation module 64 is configured to monitor and control the inflation of balloon 38. In some embodiments, inflation module 64 can use irrigation fluid to inflate balloon 38, and control the inflation of the balloon by controlling a flow rate of the irrigation fluid into the balloon. In these embodiments balloon 38 typically comprises multiple small fenestrations (not shown) that allow the irrigation fluid to exit the balloon. These fenestrations are typically 0.025-0.500 millimeters in diameter.

As is described herein, probe 22 is used to ablate elements of PV 84. However, other methods for processor 44 to ablate elements of PV 84 are also considered to be comprised within the scope of the present invention. For example, probe 22, with a distal end exemplified by distal end 26, operates as a balloon catheter, while another type of probe, such as a focal catheter, may also be used for the ablation. An example of a medical probe being formed as a focal catheter is provided in FIG. 3, as described below.

Figure 3:
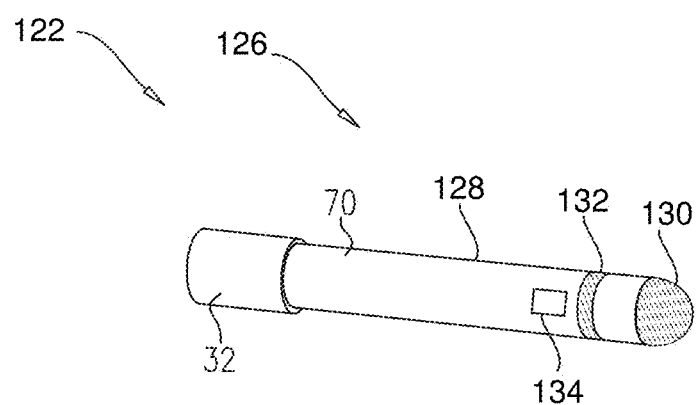
FIG. 3 is a schematic pictorial illustration of a distal end of a medical probe used in the system, according to an alternative embodiment of the present invention.

FIG. 3 is a schematic pictorial illustration of a distal end 126 of a medical probe 122, according to an alternative embodiment of the present invention. Apart from the differences described below, the operation of distal end 126 is generally similar to that of distal end 26 (FIGS. 1 and 2), and elements indicated by the same reference numerals in both distal end 26 and 126 are generally similar in construction and in operation.

In contrast to distal end 26 of probe 22, distal end 126 of probe 122 does not comprise a balloon. Rather distal end 126 is formed as a generically cylindrical extension 128 of shaft 70. At the distal tip of extension 128 an electrode 130, typically in the shape of a cup, is formed to cover the distal tip. Typically one or more other electrodes 132, typically in the form of rings, surround extension 128. As for electrodes 74, electrode 130 is configured to operate as an ablation electrode, by being coupled to ablation module 66. In addition, while electrodes 132 may also be configured to act as ablation electrodes by being coupled to module 66, they are typically configured to be similar to electrodes 48, i.e., to act as location sensors by being coupled to the current tracking module, and/or to measure electrical activity and/or provide pacing.

It will be understood that with distal end 126 probe 122 operates as a focal catheter, and the distal end may be tracked using module 46. Alternatively or additionally, distal end 126 may comprise a magnetic sensor 134, generally similar to sensor 76, in which case distal end 126 may be tracked using EM tracking module 88.

In embodiments of the present invention, in addition to probe 22 or probe 122 being used to ablate patient 30, processor 44 is coupled to a pulmonary vein isolation (PVI) module 138. Module 138, inter alia, stores a value of a $CHA_2DS_2$-VASc score for patient 30, and the $CHA_2DS_2$-VASc score is described below with reference to FIG. 4. Other functions of PVI module 138 are described with reference to the flowchart of FIG. 5.

Figure 4:
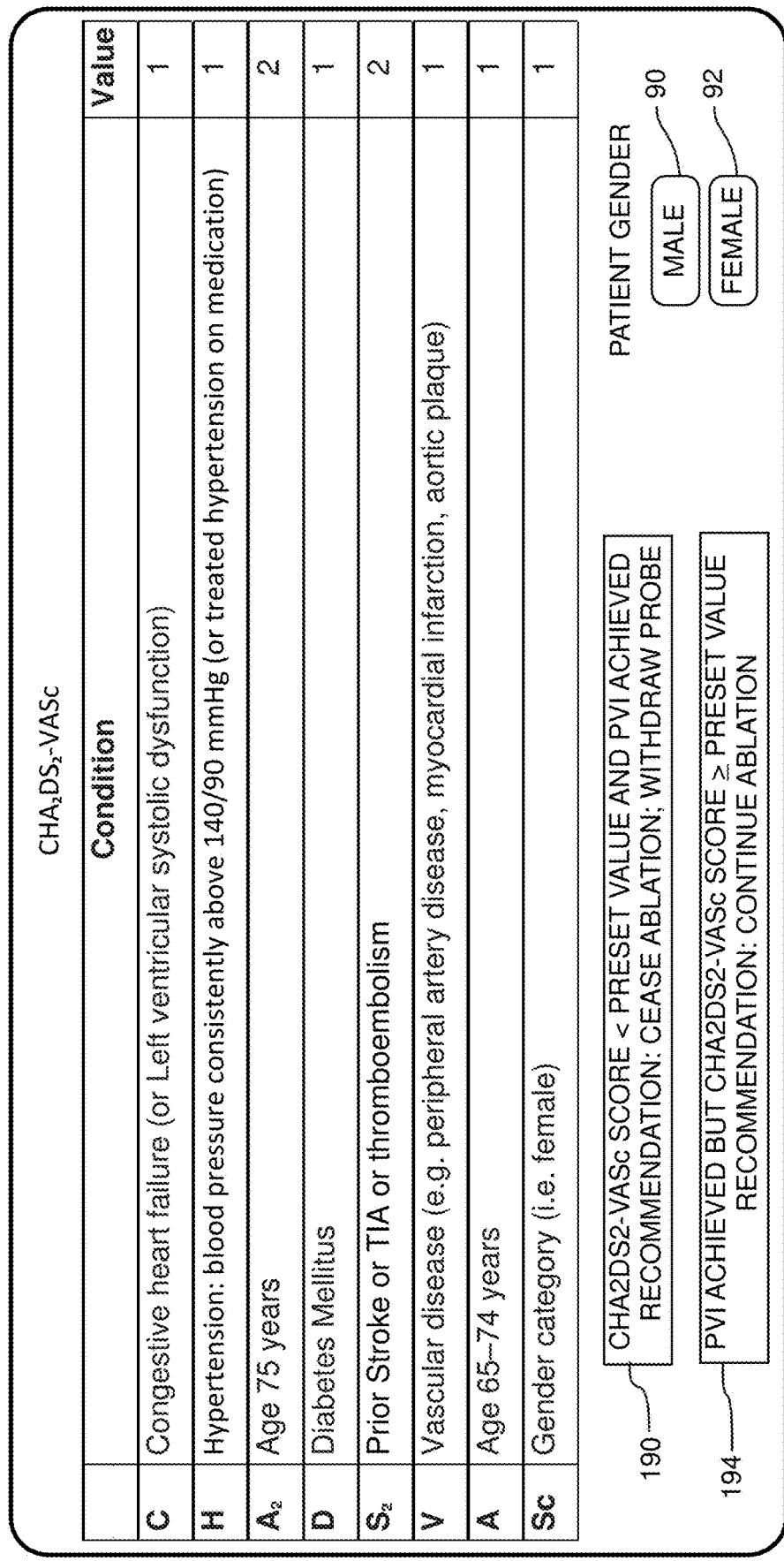
FIG. 4 is a schematic diagram illustrating a chart of $CHA_2DS_2$-VASc, according to an embodiment of the present invention.

FIG. 4 is a schematic diagram illustrating a chart 68 of $CHA_2DS_2$-VASc, as it is presented to physician 36 on display 58, according to an embodiment of the present invention.

The chart of $CHA_2DS_2$-VASc illustrates eight conditions of patient 30 that physician 36 considers, before performing ablation on the patient. Each of the conditions is assumed to be present or absent. If absent, the condition is assigned a value of zero (0). If present, the condition has a value given by Table I:

TABLE I

| Symbol | Condition | Value |
|---|---|---|
| C | Congestive heart failure (or Left ventricular systolic dysfunction) | 1 |
| H | Hypertension: blood pressure consistently above 140/90 mmHg (or treated hypertension on medication) | 1 |
| $A_2$ | Age ≥75 years | 2 |
| D | Diabetes Mellitus | 1 |
| $S_2$ | Prior Stroke or TIA (transient ischemic attack) or thromboembolism | 2 |
| V | Vascular disease (e.g. peripheral artery disease, myocardial infarction, aortic plaque) | 1 |
| A | Age 65-74 years | 1 |
| Sc | Gender category (i.e. female) | 1 |

To evaluate the $CHA_2DS_2$-VASc score for patient 30, the physician totals the values of all the conditions. For example, if patient 30 is a 60 year old male with diabetes mellitus, the $CHA_2DS_2$-VASc score is 1.

The physician may enter the value of the $CHA_2DS_2$-VASc score into PVI module 138, using controls 62. As described in the flowchart of FIG. 5, which illustrates steps of an algorithm stored in PVI module 138, the $CHA_2DS_2$-VASc score is used by the PVI module to determine how ablation of patient 30 may to be performed.

The algorithm also uses the gender of patient 30, and the physician may input the patient's gender to processor 40 by any convenient means, for instance by using touch screen buttons 90 or 92, or by selecting the appropriate button with controls 62.

Figure 5:
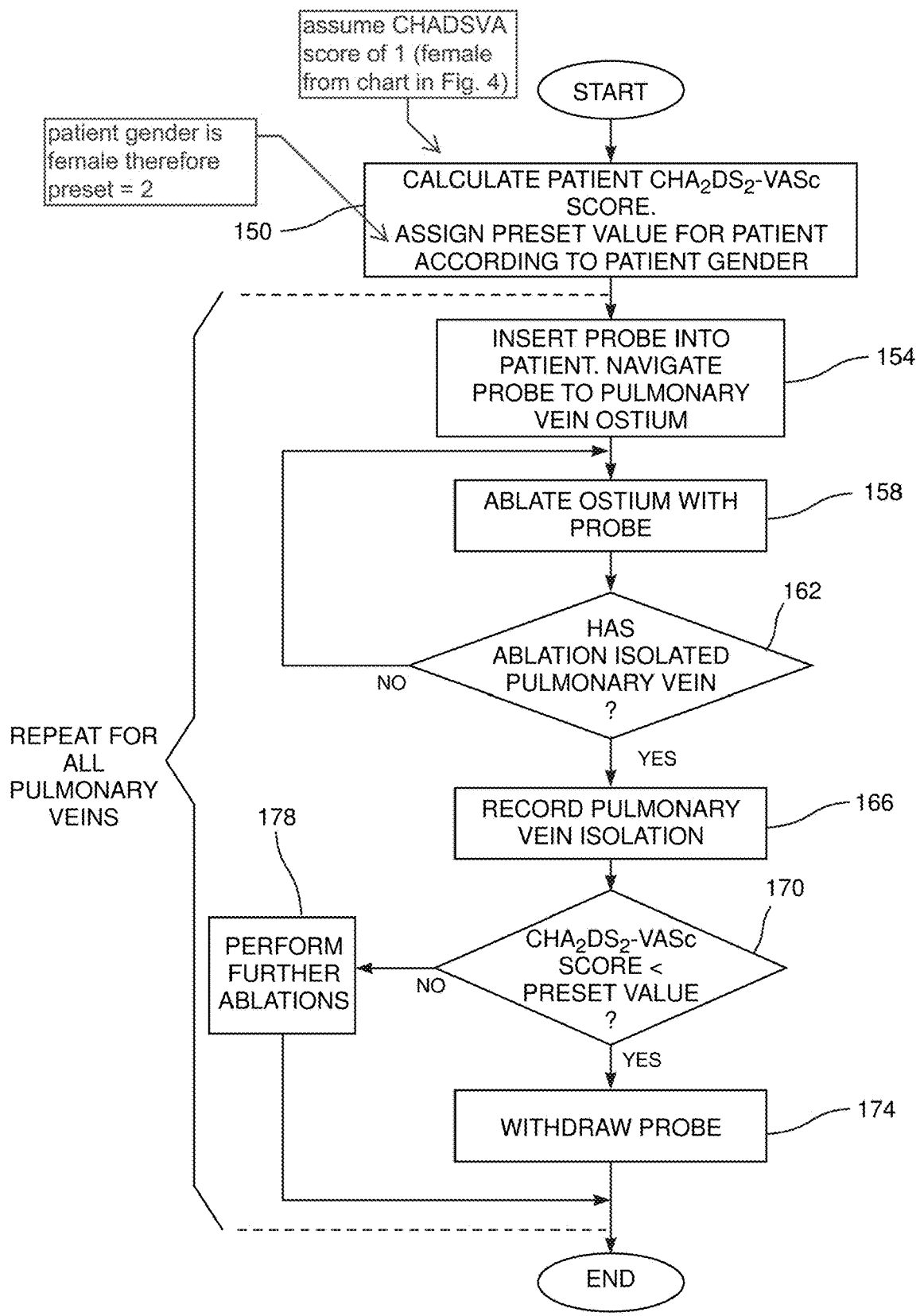
FIG. 5 is a flowchart of steps of an algorithm stored in a module of the system, according to an embodiment of the present invention.

FIG. 5 is a flowchart of steps of an algorithm stored in PVI module 138, according to an embodiment of the present invention. The algorithm is implemented by processor 40, and comprises steps of a procedure followed for ablation of patient 30, and the description assumes that probe 22 with distal end 26, i.e., a balloon catheter, is used for the procedure. The description may be modified, mutatis mutandis, for other probes, such as probe 122, i.e., a focal catheter, and the use of such other probes is considered to be comprised within the scope of the present invention.

In an initial step 150, physician 36 evaluates the $CHA_2DS_2$-VASc score of patient 30, and stores the score in module 138, as described above with reference to FIG. 4. In the initial step the physician also inputs the gender of patient, as described above, to processor 40 and the processor uses the patient's gender to assign and record a preset value for the patient. If the patient is male the preset value is assigned to be 1; if the patient is female the preset value is assigned to be 2. The preset value is used in a comparison step 170, described below.

The physician repeats the remaining steps of the flowchart for each pulmonary vein in turn, until all pulmonary veins of the patient have been treated.

In a probe insertion step 154, the physician inserts probe 22 into patient 30, and navigates distal end 26 until electrodes 74 of the distal end are in contact with ostium 82 of pulmonary vein 84. The navigation may be performed using current tracking module 46 and/or EM tracking module 88, and the contact may be verified as described above, e.g., by observing changes of impedance between electrodes 74 and patches 42.

In an ablation step 158, and using a first comparison step 162, the physician uses RF generator 86 to ablate a circle around the ostium. While performing the ablations, the physician checks if the pulmonary vein has been isolated. The check for isolation typically comprises measuring changes in impedance of the ablated tissue, and/or observing changes in signals by signal pacing and/or passive signal acquisition. If pacing is used, isolation is indicated if a signal injected on one side of the ablated circle is not observed on the other side. If passive signal acquisition is used, isolation may be indicated if signals that were present before the ablation are no longer present.

If comparison step 162 returns negative, the physician continues ablation in step 158.

If comparison step 162 returns positive, i.e., the physician has determined that the pulmonary vein is isolated, control continues to a notification step 166, where the physician notifies processor 44, using controls 62, to record isolation.

In a second comparison step 170, the processor checks if the $CHA_2DS_2$-VASc score of patient 30, stored in PVI module, is less than the preset value recorded in step 150.

If the comparison returns positive, i.e., the score is less than the preset value, then embodiments of the present invention assume that with this score and the achievement of isolation, no further ablation is necessary. In this case control continues to a withdraw probe step 174 where the physician may be recommended to cease ablation and withdraw the probe from the vein because pulmonary vein isolation has been achieved and the score is less than 2. In one embodiment the recommendation is in the form of a notice to the physician, such as a notice 190 (FIG. 4), that is presented on display 58.

If comparison 170 returns negative, i.e., the score is the preset value or more, then embodiments of the present invention assume that even given the achievement of isolation, with this score further ablation outside the pulmonary vein is necessary. In this case control continues to a further ablation step 178, where the physician may be recommended to continue ablation. In one embodiment the recommendation is in the form of a notice to the physician, such as a notice 194 (FIG. 4), that is presented on display 58.

The further ablations needed are in proximity to the pulmonary vein, and may include ablation of rotors (e.g. focal triggers having a repetitive activation pattern), ablation to isolate the posterior atrial wall, ablation to isolate the left atrial appendage, and/or ablation of additional locations of arrhythmogenic activity. It will be understood that this list is not comprehensive, and other ablations that may be needed are also considered to be comprised within the scope of the present invention.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for ablating a patient, comprising:
   (a) ascertaining a $CHA_2DS_2$-VASc score for the patient;
   (b) assigning a preset value for the patient based on a gender of the patient, the preset value being a first value if the patient is male, the preset value being a second value if the patient is female, the first and second values being different from each other, the preset value being 1 if the patient is male, and being 2 if the patient is female;
   (c) inserting a probe into the patient, so as to contact a pulmonary vein of the patient;
   (d) ablating the pulmonary vein by applying energy via the probe until pulmonary vein isolation (PVI) is achieved;
   (e) when PVI is achieved and the $CHA_2DS_2$-VASc score is less than the preset value, ceasing ablation of the pulmonary vein; and
   (f) when PVI is achieved and the $CHA_2DS_2$-VASc score is greater than or equal to the preset value, applying the energy to perform a further ablation.

2. The method according to claim 1, the probe comprising a balloon catheter.

3. The method according to claim 1, the probe comprising a focal catheter.

4. The method according to claim 1, the energy comprising radio-frequency energy.

5. The method according to claim 1, the further ablation being in proximity to the pulmonary vein.

6. The method according to claim 5, the further ablation comprising ablation of rotors.

7. The method according to claim 5, the further ablation comprising ablation to isolate a posterior atrial wall.

8. The method according to claim 5, the further ablation comprising ablation to isolate a left atrial appendage.

9. The method according to claim 5, the further ablation comprising ablation of an additional location of arrhythmogenic activity.

10. Apparatus for ablating a patient, comprising:
    (a) a probe, configured to be inserted into the patient, so as to contact a pulmonary vein of the patient; and
    (b) a processor, configured to:
        (i) ascertain a $CHA_2DS_2$-VASc score for the patient,
        (ii) assign a preset value for the patient based on a gender of the patient, the preset value being a first value if the patient is male, the preset value being a second value if the patient is female, the first and second values being different from each other, the preset value being 1 if the patient is male, and being 2 if the patient is female,
        (iii) ablate the pulmonary vein by applying energy via the probe so as to ablate the pulmonary vein until pulmonary vein isolation (PVI) is achieved,
        (iv) cease ablation of the pulmonary vein when PVI is achieved and the $CHA_2DS_2$-VASc score is less than the preset value, and
        (v) apply the energy to perform a further ablation when PVI is achieved and the $CHA_2DS_2$-VASc score is greater than or equal to the preset value.

11. The apparatus according to claim 10, the probe comprising a balloon catheter.

12. The apparatus according to claim 10, the probe comprising a focal catheter.

13. The apparatus according to claim 10, the energy comprising radio-frequency energy.

14. The apparatus according to claim 10, the further ablation being in proximity to the pulmonary vein.

15. The apparatus according to claim 14, the further ablation comprising ablation of rotors.

16. The apparatus according to claim 14, the further ablation comprising ablation to isolate a posterior atrial wall.

17. The apparatus according to claim 14, the further ablation comprising ablation to isolate a left atrial appendage.

18. The apparatus according to claim 14, the further ablation comprising ablation of an additional location of arrhythmogenic activity.

* * * * *